United States Patent
Kim

(10) Patent No.: US 7,914,284 B2
(45) Date of Patent: Mar. 29, 2011

(54) DENTAL FILING TOOL

(76) Inventor: Daniel S. Y. Kim, Vancouver, WA (US)

( * ) Notice: Subject to any disclaimer, the term of this patent is extended or adjusted under 35 U.S.C. 154(b) by 419 days.

(21) Appl. No.: 11/982,117

(22) Filed: Nov. 1, 2007

(65) Prior Publication Data
US 2008/0081313 A1  Apr. 3, 2008

Related U.S. Application Data

(63) Continuation-in-part of application No. 10/945,033, filed on Sep. 21, 2004, now abandoned.

(51) Int. Cl.
*A61C 3/06* (2006.01)
(52) U.S. Cl. ........................................ 433/142
(58) Field of Classification Search ........... 433/142, 433/148, 149; 132/321, 329
See application file for complete search history.

(56) References Cited

U.S. PATENT DOCUMENTS

| | | | | |
|---|---|---|---|---|
| 1,201,875 A * | 10/1916 | Russ | | 433/142 |
| 2,288,011 A * | 6/1942 | Mizzy | | 433/148 |
| 2,730,804 A * | 1/1956 | Saupe | | 433/142 |
| 2,736,327 A * | 2/1956 | Schlicksupp | | 132/323 |
| 2,771,085 A * | 11/1956 | Fleming | | 132/321 |
| 4,592,729 A * | 6/1986 | Bilciurescu | | 433/142 |
| 5,084,978 A * | 2/1992 | McReynolds | | 30/517 |
| 6,386,873 B1 * | 5/2002 | Blank | | 433/142 |
| 6,508,649 B2 * | 1/2003 | Grätz | | 433/142 |
| 7,455,521 B2 * | 11/2008 | Fishburne, Jr. | | 433/142 |
| 7,824,182 B2 * | 11/2010 | Kim | | 433/142 |
| 2006/0057540 A1 * | 3/2006 | Navarro | | 433/166 |
| 2006/0063131 A1 * | 3/2006 | Kim | | 433/142 |
| 2006/0127845 A1 * | 6/2006 | Khouri | | 433/142 |

FOREIGN PATENT DOCUMENTS

JP    7-194618    * 8/1995

* cited by examiner

*Primary Examiner* — Ralph A Lewis
(74) *Attorney, Agent, or Firm* — Rylander & Associates PC; Kurt M. Rylander; Mark E. Beatty

(57) ABSTRACT

A dental filing tool and method for use includes providing a unitary injection-molded handle with integral finger pads, indicia markings, and an abrasive filing strip embedded into the handle vertical arms; inserting the tool between teeth to cut and file restorations; and, disposing after use. A method for making a dental filing tool is provided, including the steps: selecting a strip; providing the strip with abrasive means; providing the strip with mounting holes; providing an injection mold with a horizontal and first and second vertical arm channels, each of the vertical arm channels having flattened opposing outer edges to form integral finger pads; and, first and second mounting pins spaced distally to hold the strip in tension; mounting the strip onto the pins within the mold; injecting plastic by injection molding means to form the dental filing tool; cooling the dental filing tool until resilient; and, removing the filing tool.

34 Claims, 5 Drawing Sheets

DENTAL FILING TOOL

CROSS-REFERENCE TO RELATED APPLICATION

This application is a continuation-in-part of and claims priority to application Ser. No. 10/945,033, filed Sep. 21, 2004 now abandoned and application Ser. No. 11/271,291, filed Nov. 12, 2005, and application Ser. No. 29/285,421, filed Mar. 28, 2007.

FIELD OF THE INVENTION

This invention relates to apparatus and methods for dental filing tools, more particularly to a dental filing tool that holds a thin abrasive filing strip which may include a cutting edge for efficient filing of the interproximal area and fitting of dental crowns, bridges, onlays, inlays and fillings, and methods to use and manufacture a dental filing tool.

BACKGROUND

The current conventional method for fitting dental crowns, bridges, onlays and inlays, herein referred to generally as restorations, involves the dental practitioner sliding colored carbon paper, of which the thickness is the recommended measured distance between teeth, between the interproximal area of the tooth and the restoration. The carbon paper marks with carbon ink the proximal contact area where the two surfaces of the teeth and/or restoration are too close, and then the practitioner grinds the restoration with a rotary instrument to remove excess material. This method is tedious, inefficient, and inexact. The dental practitioner has to continually remove the restoration and grind the heavy proximal contact surface until the fitting surface and shape is achieved, at which point the restoration may be permanently fixed. It is a time consuming process and there is possibility of over-grinding, in which case a new restoration must be reconstructed to replace it. This involves significant expense of time and money, not to mention inconvenience for the patient who suffers for the delay and agony.

Another method employed is the stand alone use of a metal filing strip coated with some superfine abrasive material. The metal filing strip is inserted between the interproximal area to file down the proximal contact area of the crown for an accurate fit. Since the space between the tooth and the crown, bridge, onlay, and inlay must not be too close nor too spaced apart the practitioner must file incrementally. These steps are repeated until the desired distance between the tooth and the restoration is achieved. Because the filing strip is extremely thin, narrow, and malleable, it is necessary for the practitioner to maintain tension in the strip by holding it taunt at opposite ends with fingers from both hands. Unfortunately holding the filing strip in such as manner is cumbersome in the patient's mouth and impedes the practitioner from achieving desired angles and restricts range of motion to effectively file. Especially when the patient is receiving crowns, bridges, onlays, or inlays in the back of the mouth where it is considerably more difficult to access, it is difficult for the practitioner to file since both hands are needed to hold tension in the strip and often a patient's mouth is too small or cannot open wide enough to accommodate the file comfortably. As a result, the patient must endure strenuous stretching of the lips and jaw area. Often a practitioner struggles to find the best placement for fingers to pinch the strip to create sufficient tension while attempting to minimize the restricting presence of both hands in the patient's mouth. This method is inefficient, tiresome for the practitioner, and uncomfortable for the patient. Moreover, because of the difficulty involved handling the filing strip, often patients sustain suffer small cuts due to the sharp edges of the strip coming in contact with gums and lips while filing the tooth or restoration.

Another method employed is that a thin metal strip coated with fine abrasive material is fastened to a removable bow which is attached a handle. Generally, the bow and handle are too long to maneuver in the mouth and limit the size of abrasive strip which is actual working surface and results ineffective in the mouth for posterior teeth. Replacing the filing strip after each use is also a hassle for the dental staff due to the fact that disassembly and assembly involve extremely small fasteners and tools. Compression on the ends of the bows will tend to loosen and pop off removable filing strips.

In order to solve the existing problems with the current methods for interproximal grinding and adjustment between restorations and teeth, it is the object of the present invention to provide a tool which has a body that secures a filing strip with sufficient tension which can be held by one hand between opposable fingers. This allows for the practitioner to maneuver within the patient's mouth with easier reach and greater range of motion for more time efficient and effective filing and grinding of the interproximal area with greater comfort for the patient for a quicker fitting of crowns, bridges, onlays, and inlays.

In addition to these inefficiencies many areas of the world lack high technology powered dental equipment and extensive training for dentists and dental assistants. Thus, the process of using powered tools to shape reconstructions out of the mouth are often not available, and such dentists are in need of an inexpensive, safe and reliable means of filing restorations and fillings in-situ.

A number of devices have provided abrasive surfaces for filing crowns, but lack the safety, control and ease of manufacture of the present invention. None of the known body of art, taken either singularly or in combination, is seen to describe the instant invention as claimed.

U.S. Pat. No. 6,386,873 to Blank teaches a filing tool with a Y-shaped handle with bosses on the ends to hold a filing blade, which is mounted by squeezing together the handle ends to hang the blade on the bosses through mounting holes. Blank does not teach a filing strip which is integrally mounted to a handle. Blank teaches a device which purports to be ergonomic for the user, which is an improvement to a degree. However, the user has to grasp the Blank device at the prongs in order to exert sufficient lateral force to be useful. Grasping Blank at the prongs would naturally tend to compress them together, creating a serious danger that the blade would separate. In addition, comparing the handle length required to form the Y-shape and provide the extended portion intended for gripping (see Blank, FIG. 1, #22), the Blank apparatus is actually quite large and clumsy for use inside a patient's mouth.

U.S. Pat. No. 2,730,804 to Saupe teaches a dental filing tool which uses a replaceable filing blade which slides into a jointed holder. The filing blade is gripped only along one side and not held in tension in the axis of the working surface. This limits the amount of lateral pressure which can be applied, and creates a danger where if the filing blade was used in a tight-fitting area the blade would either displace or bend. Saupe does not teach tapering and rounding the inner edges of the blade holder to allow the blade handle to fit comfortably against the gap between teeth without causing damage.

Japan Patent 593138377 (the JP '377 patent) teaches a dental filing tool with a U-shaped handle and filing strip.

However, JP '377 teaches a replaceable filing strip mounted on pegs or bosses, rather than an embedded strip (see JP '377, FIGS. 3 and 7, #7). There is therefore a significant danger that the blade could separate during use in a patient's mouth. Applying lateral or longitudinal pressure during use naturally causes the user to squeeze the handle together which would loosen the blade and likely cause it to pop off. In addition, if the filing strip hit a difficult or tight area there is substantial risk that it might simply deform and tear off the pegs. This danger could be lessened by angling the pegs (#7) away from each other, but this would make assembly by dental staff very difficult, especially considering the small size of the parts. Nor does JP '377 disclose tapered inner edges to better fit within the facial and lingual embrasures between adjacent teeth, nor integral fingerpads for gripping.

Injection molding provides the ability to manufacture filing tools with non-removable filint strips so as to avoid danger of separation due to poorly designed or poorly assembled blade retention means. One can also thereby manufacture filing tools with tension built into the abrasive strip. Injection mold manufacturing techniques reduce cost sufficiently that the dental filing tools may be considered disposable. Disposing of the tools for recycling of the plastic and metal, rather than requiring dental staff to disassemble and replace abrasive strips, saves significant labor and supervision burdens, and prevents mistakes in assembly from causing harm to patients. The present invention solves these problems.

Thus, while the foregoing body of art indicates it to be well known to have a dental filing tool, the known art does not teach or suggest a dental filing tool which has the following combination of desirable features: (1) small enough to be held between two fingers by the user; (2) able to hold a filing strip securely without risk of separating in a patient's mouth; (3) inexpensively produced so as to be essentially disposable; (4) tensioned so as to be rigid enough to permit lateral pressure during both forward and reverse movement but still flexible so as to conform to concave/convex surfaces in the interproximal areas of teeth; (5) allows for easy and effective disinfection; and, (6) allows for easy and simplified labelling and indexing of filing blades; (7) tapered inner edges for comfortable fit into the facial and lingual embrasures; (8) includes integral fingerpads for easier control and efficient manufacture.

SUMMARY AND ADVANTAGES

A disposable dental filing tool is provided and includes a handle with a horizontal arm with a first vertical arm attached at a first end and a second vertical arm attached at second a end forming an arch structure; a filing strip with first and second ends attached to the handle at the first and second vertical arms, suspended therebetween with tension; and wherein the vertical arms have flattened fingertip end pads to allow for holding the handle between opposing fingertips.

A method for using a disposable dental filing tool is provided and includes providing an injection molded handle having a horizontal arm, which tapers from its top edge downwards to a beveled edge and which has a raised horizontal middle flat on each lateral side of said arm, and two vertical arms, each of which tapers from its outside edges inwards to a beveled edge, to form an rectangular arch, with a filing strip embedded within the vertical arms of the handle during the injection molding process; inserting the filing strip between teeth or between teeth and restorations by holding the handle at the raised middle flats of the horizontal arm between opposing fingertips; cutting and filing said teeth and restorations with a grinding and sawing motion; and disposing of said dental filing tool after use. A method of using a dental filing tool can include providing an injection molded handle having a horizontal arm, which tapers from its top edge downwards to a beveled edge and which has a raised horizontal middle flat on each lateral side of said arm, and two vertical arms with integral fingertip pads on their outside edges, each of which tapers from its outside edges inwards to a beveled edge, to form an rectangular arch, with a filing strip embedded within the vertical arms of the handle during the injection molding process; inserting the filing strip between teeth or between teeth and restorations by holding the handle at the raised middle flats of the horizontal arm between opposing fingertips; cutting and filing said teeth and restorations with a grinding and sawing motion; and disposing of said dental filing tool after use.

A method for manufacturing a dental filing tool includes the steps of: selecting a strip of desired thickness, said strip including a front surface and a back surface, a first distal end and a second distal end, and a top edge and a bottom edge; providing said strip with an abrasive surface or pattern; providing said strip with mounting holes through said first and second distal ends of said strip; providing an injection mold, said injection mold including: a cavity including a horizontal arm channel, first and second vertical arm channels extending from said horizontal arm channel with corresponding first and second projecting ends, each of said vertical arm channels being tapered toward their inner edges and having flattened opposing outer edges extending along at least a portion of the length of said vertical arm channels, so as to form integral opposing finger pads on said filing tool; and, first and second mounting pins located within said first and second projecting ends of said first and second vertical arm channels, wherein the cross sectional areas of said mounting pins are less than the cross sectional areas of said mounting holes, and wherein said first and second mounting pins are spaced distally to hold said strip in tension; mounting said strip onto said first and second mounting pins through said mounting holes within said mold; injecting plastic into said mold by injection molding, such that said plastic flows around the ends of said first and second distal ends of said strip and through said first and second mounting holes, to form the dental filing tool; cooling said dental filing tool until said plastic is resilient; removing said dental filing tool from said mold.

A dental filing tool is provided and includes a unitary handle, formed from injection-molded plastic, having a horizontal arm including top and bottom edges and first and second ends, with first and second vertical arms extending from said first and second ends, said vertical arms including corresponding first and second projecting ends, wherein the cross-sections of at least said first and second vertical arms are tapered toward their inside edges; opposing first and second finger pads formed into said unitary plastic handle at said first and second ends for gripping said filing tool, said finger pads at least partially extending along the outer edges of said first and second vertical arms, and, inidicia markings on said horizontal arm, and, a stainless steel filing strip including front and back surfaces, first and second mounting holes at the distal ends of said filing strip, and abrasive means disposed along said filing strip; wherein said filing strip spans between said first and second vertical arm projecting ends, with said first and second mounting holes embedded within said first and second vertical arm projecting ends.

The disposable dental filing tool of the present invention presents numerous advantages, including: (1) small enough to be held between two fingers by the user; (2) able to hold a filing strip securely without risk of separating in a patient's mouth; (3) inexpensively produced so as to be essentially disposable; (4) tensioned so as to be rigid enough to permit lateral pressure during both forward and reverse movement but still flexible so as to conform to concave/convex surfaces in the interproximal areas of teeth; (5) allows for easy and effective disinfection; and, (6) allows for easy and simplified labelling and indexing of filing blades; (7) tapered inner edges for comfortable fit into the facial and lingual embrasures; (8) includes integral fingerpads for easier control and efficient manufacture. Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims. Further benefits and advantages of the embodiments of the invention will become apparent from consideration of the following detailed description given with reference to the accompanying drawings, which specify and show preferred embodiments of the present invention.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

DETAILED DESCRIPTION

Figure 1:
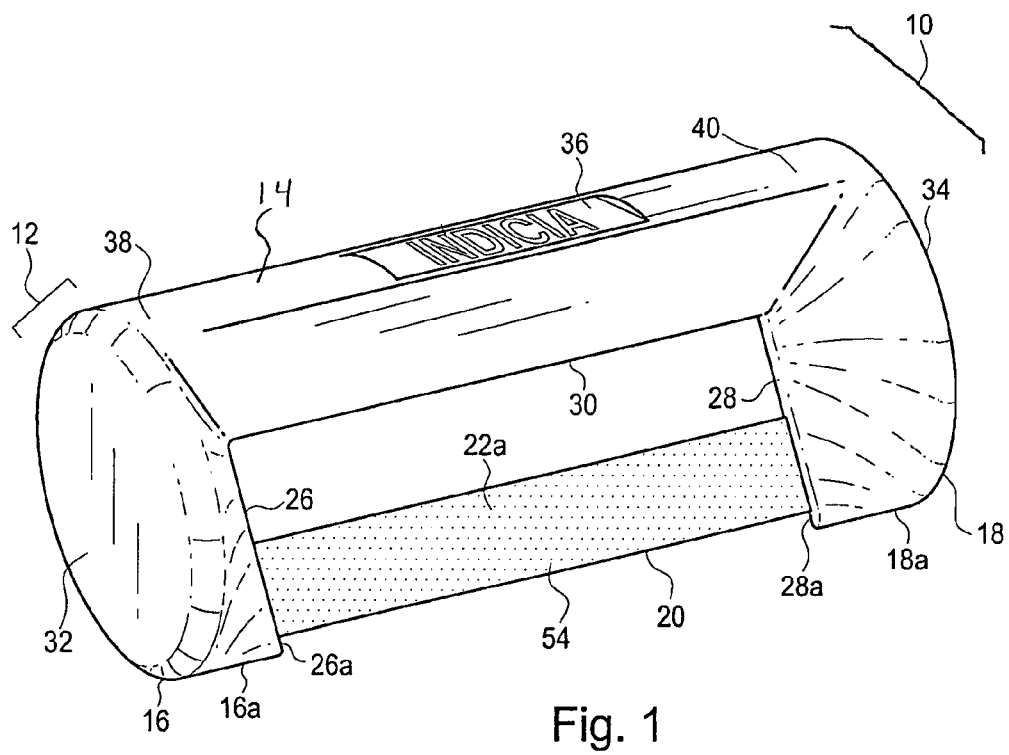
FIG. 1 is a perspective view of an embodiment of Applicant's invention.
Figure 2:
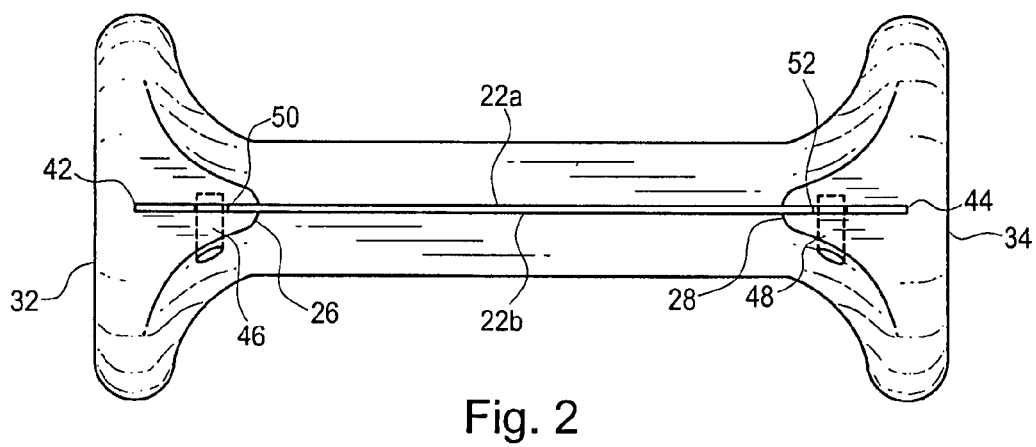
FIG. 2 is a bottom view of the embodiment shown in FIG. 1.
Figure 3:
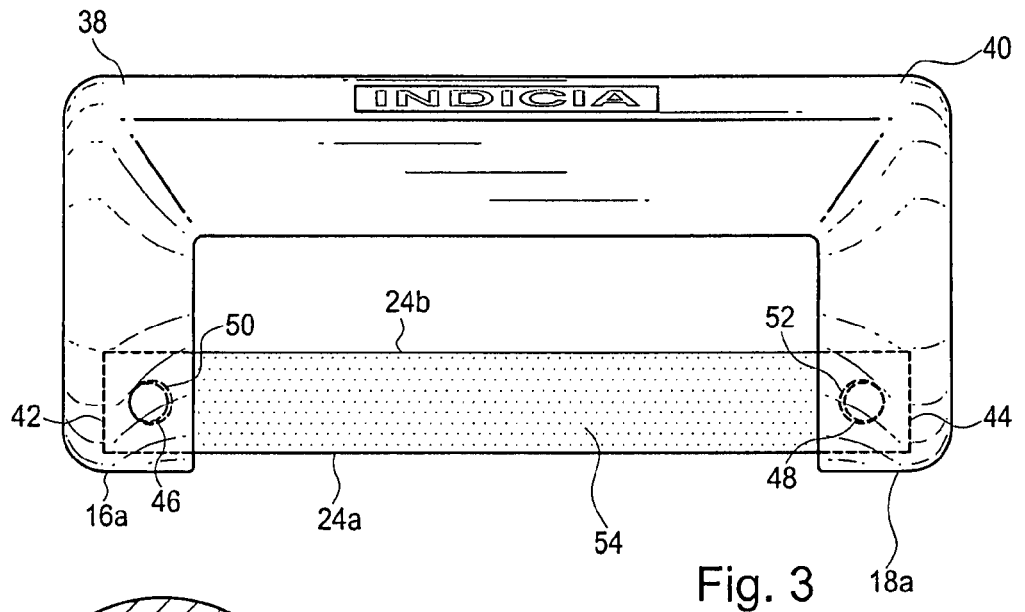
FIG. 3 is a front view of the embodiment shown in FIG. 1.
Figure 4:
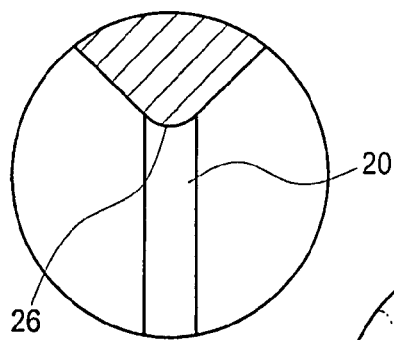
FIG. 4 is a partial sectional view of the embodiment shown in FIG. 1.

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

A disposable dental filing tool is provided, comprising a handle including a horizontal arm with a first vertical arm attached at first end and a second vertical arm attached at second end forming an arch structure; a filing strip with first and second ends attached to said handle at said first and second vertical arms, suspended therebetween with tension; and wherein said vertical arms have flattened fingertip end pads to allow for holding the handle between opposing fingertips.

A method for using a disposable dental filing tool is provided and includes providing an injection molded handle having a horizontal arm, which tapers from its top edge downwards to a beveled edge and which has a raised horizontal middle flat on each lateral side of said arm, and two vertical arms, each of which tapers from its outside edges inwards to a beveled edge, to form an rectangular arch, with a filing strip embedded within the vertical arms of the handle during the injection molding process; inserting the filing strip between teeth or between teeth and restorations by holding the handle at the raised middle flats of the horizontal arm between opposing fingertips; cutting and filing said teeth and restorations with a grinding and sawing motion; and disposing of said dental filing tool after use. A method of using a dental filing tool can include providing an injection molded handle having a horizontal arm, which tapers from its top edge downwards to a beveled edge and which has a raised horizontal middle flat on each lateral side of said arm, and two vertical arms with integral fingertip pads on their outside edges, each of which tapers from its outside edges inwards to a beveled edge, to form an rectangular arch, with a filing strip embedded within the vertical arms of the handle during the injection molding process; inserting the filing strip between teeth or between teeth and restorations by holding the handle at the raised middle flats of the horizontal arm between opposing fingertips; cutting and filing said teeth and restorations with a grinding and sawing motion; and disposing of said dental filing tool after use.

A method for manufacturing a dental filing tool, comprises the steps of: selecting a strip of desired thickness, said strip including a front surface and a back surface, a first distal end and a second distal end, and a top edge and a bottom edge; providing said strip with abrasive means; providing said strip with mounting holes through said first and second distal ends of said strip; providing an injection mold, said injection mold including: a cavity including a horizontal arm channel, first and second vertical arm channels extending from said horizontal arm channel with corresponding first and second projecting ends, each of said vertical arm channels being tapered toward their inner edges and having flattened opposing outer edges extending along at least a portion of the length of said vertical arm channels, so as to form integral opposing finger pads on said filing tool; and, first and second mounting pins located within said first and second projecting ends of said first and second vertical arm channels, wherein the cross sectional areas of said mounting pins are less than the cross sectional areas of said mounting holes, and wherein said first and second mounting pins are spaced distally to hold said strip in tension; mounting said strip onto said first and second mounting pins through said mounting holes within said mold; injecting plastic into said mold by injection molding means, such that said plastic flows around the ends of said first and second distal ends of said strip and through said first and second mounting holes, to form the dental filing tool; cooling said dental filing tool until said plastic is resilient; removing said dental filing tool from said mold.

A dental filing tool is provided and includes a unitary handle, formed from injection-molded plastic, having a horizontal arm including top and bottom edges and first and second ends, with first and second vertical arms extending from said first and second ends, said vertical arms including corresponding first and second projecting ends, wherein the cross-sections of at least said first and second vertical arms are tapered toward their inside edges; opposing first and second finger pads formed into said unitary plastic handle at said first and second ends for gripping said filing tool, said finger pads at least partially extending along the outer edges of said first and second vertical arms, and, inidicia markings on said horizontal arm, and, a stainless steel filing strip including front and back surfaces, first and second mounting holes at the distal ends of said filing strip, and abrasive means disposed along said filing strip; wherein said filing strip spans between said first and second vertical arm projecting ends, with said first and second mounting holes embedded within said first and second vertical arm projecting ends As shown in FIGS. 1-5, a dental filing tool 10 is provided and includes a unitary plastic handle 12 formed by injection molding, with a horizontal arm 14 having a first end 38 and a second end 40, with a first vertical arm 16 and second vertical arm 18 extending perpendicularly from horizontal arm 14. Vertical arms 16 and 18 include projecting ends 16a and 18a respectively. The cross-sections of first and second vertical arms 16 and 18 are tapered inwardly toward their inner edges 26 and 28 respectively. This taper allows full range of motion by fitting into the facial and lingual embrasures between adjacent teeth. Inner edges 26 and 28 may be radiused for greater comfort when the tool handle 12 contacts with gum surfaces during use. Horizontal arm 14 may also taper to inner edge 30. Unitary handle 12 includes opposing integral first and second finger pads 32 and 34 respectively which extend at least partially along the outer edges of first and second vertical arms 16 and 18. Horizontal arm 14 may include indicia 36 which can be used to identify the size and abrasive portion of the filing strip 20. Indicia 36 may also include a trademark or other identifying mark.

Figure 9:
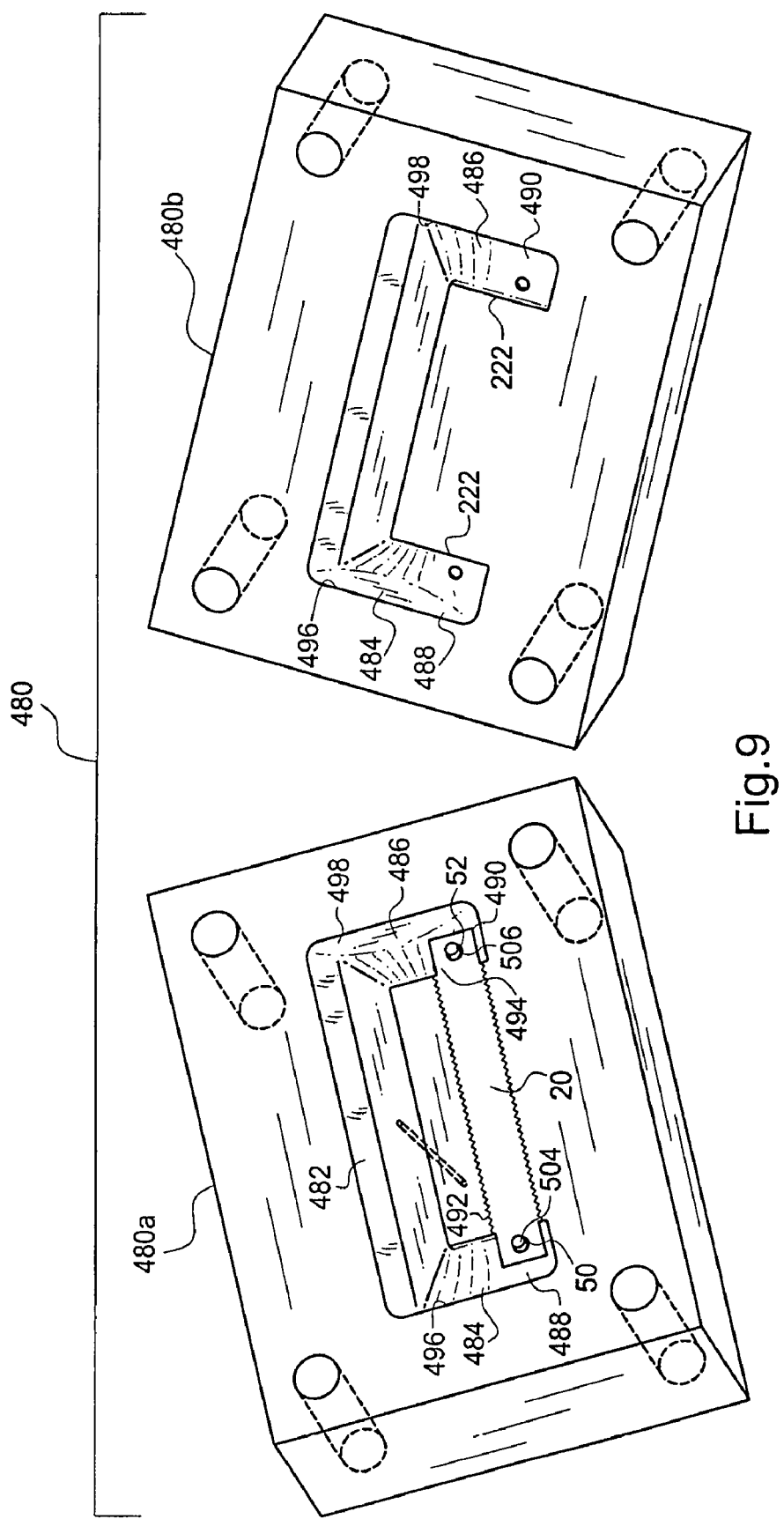
FIG. 9 is perspective view of injection molding blocks useful in a method for manufacturing a filing tool.

Filing strip 20 includes front and back surfaces 22a and 22b, bottom and top edges 24a and 24b, and first and second mounting holes 50 and 52 at corresponding first and second distal ends 42 and 44. Filing strip 20 spans across from first projecting end 16a to second projecting end 18a. Plastic handle 12 is formed with filing strip ends 42 and 44 embedded within projecting ends 16a and 18a. During the injection molding process plastic will flow through the unblocked space between mounting holes 50 and 52 and their respective mounting pins 504 and 506 (see FIG. 9), and around filing strip distal ends 42 and 44, to completely enclose and engage filing strip 20. Abrasive coating 54 is disposed on one or both of front and back surfaces 22a and 22b to provide an abrasive surface, with grit size in the range of 200 to 900 grit (200 being more coarse and 900 being more fine). Preferably abrasive coating 54 is diamond dust or equivalently hard grit material to enable abrasion of hard tooth enamel and epoxies used in dental restorations. Preferably the abrasive portion 54 of filing strip 20 does not extend into the portion of filing strip 20 which is embedded within projecting ends 16a and 18a so that a separate injection mold does not have to be designed for each abrasive type, thereby saving significant costs—an important factor considering that the dental filing tool 10 is intended to be inexpensive and essentially disposable. Filing strip 20 is preferably made from stainless steel, which is commonly used for medical devices for its durability, strength, non-porosity and ability to withstand autoclave sterilization. Filing strip 20 may also be made from titanium or other suitable materials as well which are of adequate strength but are not subject to corrosion. Filing strip 20 thickness is preferably selected to be in the range of 0.04 mm to 0.12 mm (0.0016 to 0.0047 inches). This range ensures filing strip 20 is narrow enough to fit between most teeth and to remain flexible, but thick enough to provide sufficient strength for removing material and to prevent kinking when used in tight spaces. Filing tools are preferably provided in several thicknesses from which a dentist may select a filing tool appropriate for the specific patient and procedure. Filing strip 20 is preferably about 3.5 mm (0.138 inches) wide to be compatible with most teeth.

Figure 6:
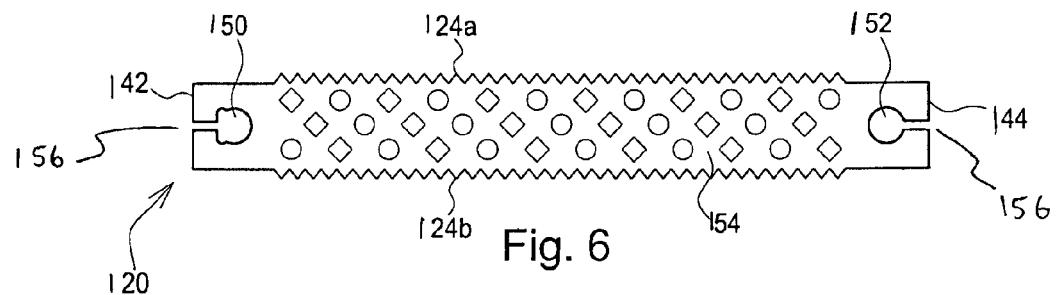
FIG. 6 is a view of a filing strip of an embodiment of the invention.

As shown in FIG. 6, filing strip 120 may include slots 156 extending from either or both of mounting holes 150 and 152 to their respective distal ends 142 and 144 in order to simplify the task of mounting filing strip 120 onto mounting pins 504 and 506 (see FIG. 9) through mounting holes 150 and 152. A pattern of perforations 154 is provided along a portion of filing strip 120 for an abrasive surface.

Figure 7:
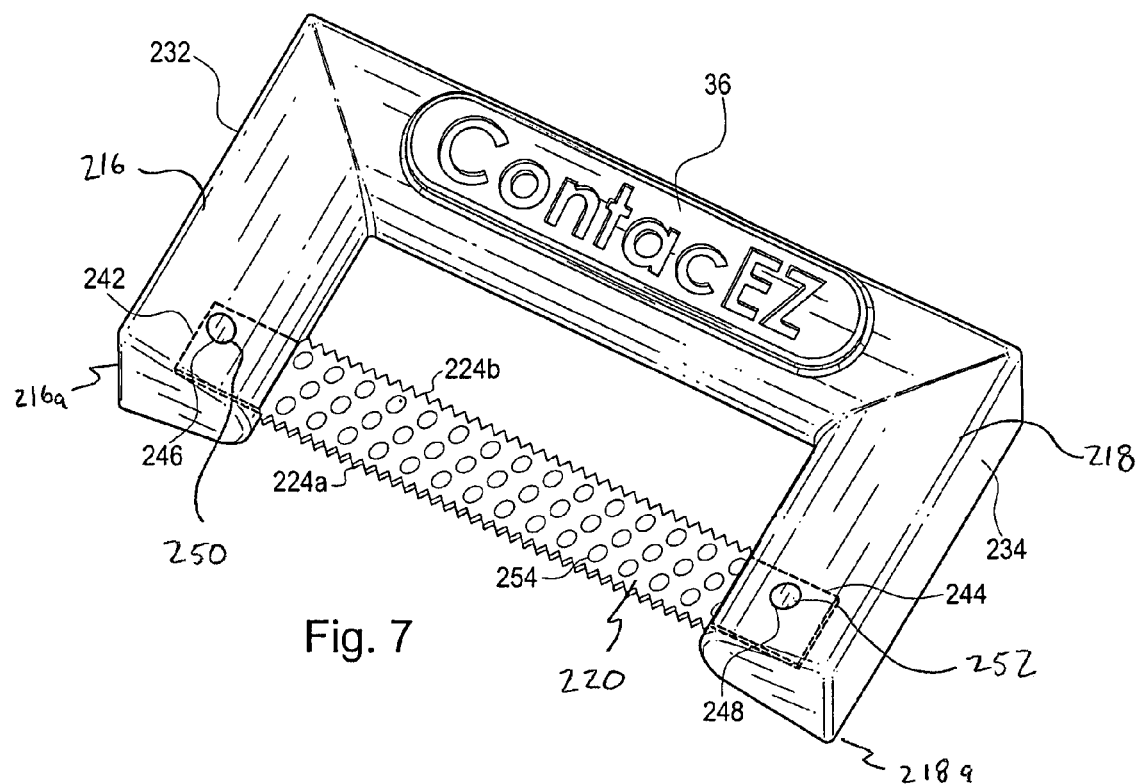
FIG. 7 is a perspective view of an embodiment of Applicant's invention.

As shown in FIG. 7, another embodiment includes a filing strip 220 with either or both of bottom and top edges 224a and 224b serrated to provide a cutting edge for separating teeth. Serrations 224a and/or 224b allow a dentist to cut through areas where filling or restoration material has completely or nearly completely occluded the interproximal area between adjacent teeth. Occasionally a patient's teeth are naturally so close together that a dentist may have to use a serrated strip 220 to separate the teeth first in order to then abrade material for the procedure. Additionally, a situation may arise where a filing strip removes a narrow band of material from a tooth surface, thereby creating a small ridge above or below the removal area. Serrated edges 224a & b allow the dentist to remove material above and/or below this band to provide equal removal along the vertical surface of the tooth.

Serrated edges 224a & b provide removal at the edges of the perforations 254. Without serrated edges 224a & b the perforations would be able to remove only a limited amount of material because the edge band, lacking perforations to remove material, would limit the depth. Thus, only smoothing or polishing would be available, whereas adding serrations permits removal of material to greater depths when needed.

Vertical arms 216 & 218 extend from horizontal arm 214. Fingerpads 232 & 234 are formed into vertical arms 216 & 218 and extend at least partly along their length—in this case they extend the entire length. Fling strip distal ends 240 & 242 with mounting holes 246 and 248 are embedded into vertical arm ends 216a & 218a. In this embodiment indicia 236 is raised on both sides of horizontal arm 214, which effectively thickens horizontal arm 214 to increase rigidity.

Figure 8A:
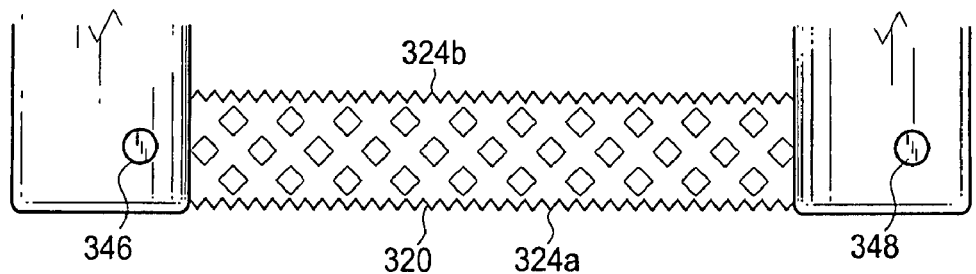
FIG. 8*a-c* are partial views of embodiments of Applicant's invention showing various filing strips.
Figure 8B:
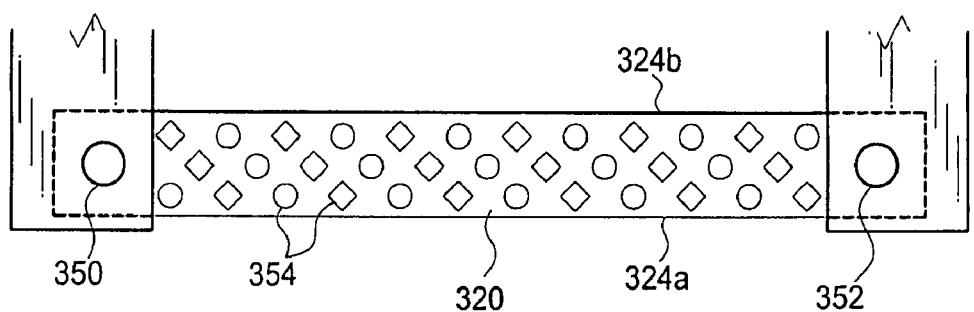
Figure 8C:
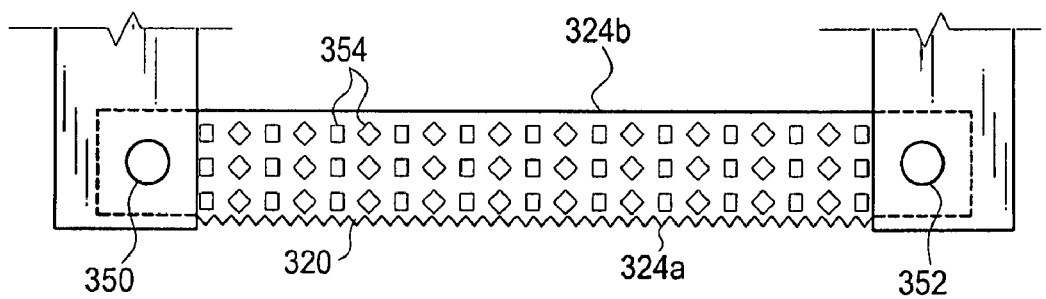

As shown in FIGS. 8a-c, perforation pattern 354a-c distributed along the length of filing strip 320 may be either unitary perforation shapes, or a plurality of perforation shapes, with perforations aligned or overlapping, and may include and may include differing combinations of edge styles 324a & b. Overlap helps to prevent bands from developing in the abraded surface. As shown in FIGS. 8a & b, perforations may overlap in the range ⅓ to ⅔ of their cross-sections to provide smoother removal. Where no overlap is present (e.g. see FIG. 8c) a dentist should alternate the axis of motion frequently to ensure smooth removal. Varying perforation shapes provide different cutting profiles for the dentist to choose from. Preferably the perforation shapes are round, diamond, or rectangular. Round perforations include circular holes and oval holes. Diamond perforations are preferably symmetrical parallelograms with at least one apex oriented in the lengthwise axis of filing strip 320. Rectangular perforations are oriented with a flat edge perpendicular to the lengthwise axis of filing strip 320. In an embodiment a perforation pattern 354b includes alternating groups of round perforations and diamond perforations, as shown in FIG. 8b. Alternating groups of perforations present different cutting profiles continuously, thereby providing more effective removal and smoothing.

As shown in FIGS. 1-5 and 9, projecting ends 16a and 18a have indentations 46 and 48 extending partially through, which are a by-product of the injection molding process. During fabrication, filing strip 20 is mounted on mounting pins 504 and 506 under tension, with mounting holes 50 and 52 being larger than 504 and 506. This gap allows plastic to flow through to strengthen the attachment of filing strip 20.

As shown in FIGS. 1-6 and 9, a method for making a dental filing tool includes the steps of selecting a filing strip 20 of desired thickness, providing filing strip 20 with abrasive portion 54, providing filing strip 20 with mounting holes 50 and 52 through distal ends 42 and 44, providing an injection mold 480 with two mirrored blocks 480a & b, each with cavities including horizontal arm channel 482, first and second vertical arm channels 484 and 486 extending from horizontal arm channel 482, with corresponding first and second projecting ends 488 and 490, vertical arm channels 484 and 486 being tapered toward their inner edges 492 and 494 and having flattened opposing outer edges 496 and 498 extending along at least a portion of the length of vertical arm channels 484 and 486 to form integral opposing first and second finger pads 32 and 34, first and second mounting pins 504 and 506 located within first and second projecting end channels 488 and 490, mounting filing strip 20 onto first and second mounting pins 504 and 506 through mounting holes 50 and 52 within mold 480, injecting plastic into mold 480 to form dental filing tool 10, cooling the tool until the plastic is resilient and is able to maintain its form, and removing the tool from mold 480. A preferred method may include the steps of cleaning the newly fabricated dental filing tool 10, sterilizing the dental filing tool and packaging the dental filing tool in sterile packaging so that it is ready for use without further assembly or cleaning. The cross-sectional area of mounting pins 504 and 506 is less than mounting holes 50 and 52, allowing plastic to flow through the unblocked area during injection molding to provide better engagement of filing strip 20. Plastic also flows around the ends of distal ends 42 and 44 to ensure that ends 42 and 44 are fully embedded within projecting ends 16a and 18a. Mounting pins 504 and 506 are spaced to engage mounting holes 50 and 52 at their distal points so as to hold filing strip 20 in tension during the injection molding process. This ensures filing strip 20 is properly embedded in the plastic and properly aligned, with no bowing of the strip.

Filing strip 20 is preferably a stainless steel strip selected in the range of 0.04 mm to 0.12 mm (0.0016 to 0.0047 inches) thick. Filing strip 20 includes front surface 22a, back surface 22b, first distal end 42, second distal end 44, top edge 24b and bottom edge 24a. Filing strip 20 is provided with abrasive portion 54 by coating either or both of front and back surfaces 22a & b with diamond dust in the range of 200 to 900 grit, or by imposing a pattern of perforations 154 into filing strip 20 along its length. Perforations 154 may be imposed by known methods such as stamp and die or equivalent methods. Perforations 154 may be a pattern including a combination of one or more shapes, including round, diamond and rectangular. Round shapes include circular and oval shapes. Diamond includes parallelograms with an apex oriented in the lengthwise direction of filing strip 20. Preferably abrasive portion 54 does not extend to the portion of filing strip 20 which is embedded into projecting ends 16a and 18a. This allows a single injection mold to be used for a given thickness of filing strip regardless of abrasive means. Otherwise, a new mold would be required for each type of abrasive means and even each grit size for diamond dust. Filing strip 20 may be provided with serrated edges along either or both of bottom and top edges 24a & b. Filing strip 20 may be provided with a slot extending from mounting holes 50 and 52 to their respective distal ends 42 and 44, to make placement of filing strip 20 onto mounting pins 504 and 506 easier, especially using automated manufacturing methods. Filing strip 20 may thereby be more easily slipped onto one of mounting pins 50 or 52 to provide alignment for placing the opposite mounting hole onto its corresponding mounting pin.

Injection molding methods are well known. However, previous dental filing tools have not been produced with a filing strip embedded into an injection molded handle during the injection molding process. In general, injection molding involves machining or etching open cavities into opposing block faces, which are then locked together forming a closed cavity into which molten plastic is injected. Common materials for molds are steel, aluminum, and ceramic. Copper and brass are sometimes used for lower temperature and pressure processes. For small items of simple design spark removal techniques are commonly used to etch the cavities, but other methods are also used and in no way limit the present invention. The opposing blocks are locked together to form the "mold" with the closed cavity inside. A single large block may include a plurality of cavities to make multiple parts simultaneously. If existing parts are to be built into the molded plastic piece, e.g. filing strip 20, then they must be mounted inside one of the blocks before the mold is clamped shut. Plastic is generally injected by feeding plastic pellets through a hopper into a screw pump with continuously decreasing pitch into the closed cavity. As the plastic moves through the screw pump it is compressed and heats up, eventually to its melting temperature. The pump cavity may also be heated to assist the melting process. The channel from the screw discharge to the cavity may be heated to maintain the plastic at its optimum temperature and viscosity during injection. Vacuum is sometimes applied to the cavity to increase the injection rate and/or prevent gas bubble formation. Following injection the injected plastic is allowed to cool, or the mold is force-cooled using cooling channels, and when cooled the mold is opened, with the newly formed part embedded in one of the blocks. The part is then removed from the block by using pusher pins built into the mold or by compressed air or nitrogen, or other known methods. The newly formed part may require trimming or smoothing after removal to meet quality specifications. The part can then be cleaned, sterilized and packaged in sterile packaging so that it can be shipped to the customer in a ready-to-use condition, either individually or as part of a kit of dental filing tools with a selection of filing strip thicknesses, abrasive types, and serrated or unserrated edges.

Figure 5:
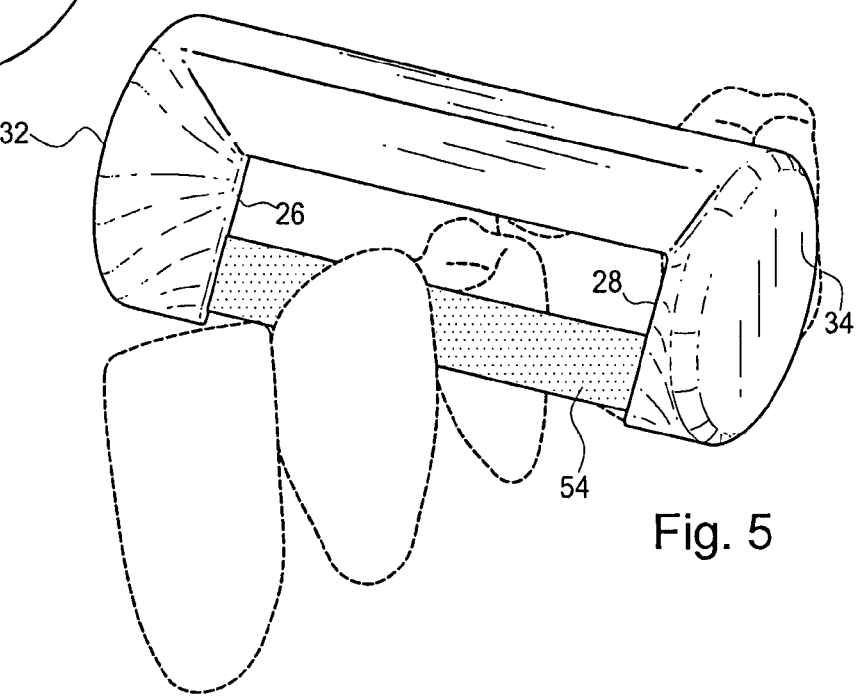
FIG. 5 is a perspective view of the embodiment shown in FIG. 1 in use showing an elevational view depicting the insertion of the filing tool interproximally

In operation, a dental filing tool 10 is held by the dental operator between the thumb and finger using opposing finger pads 32 & 34. Filing strip 20, with abrasive portion 54, is inserted into the interproximal area and worked back and forth (as shown in FIG. 5), with pressure applied laterally, to remove material and shape the tooth surface before or after the application of fillings or dental reconstructions. A dental filing tool including serrated edges, e.g. FIG. 7 #224a, may be used to separate teeth where reconstruction material has inadvertently bonded two teeth together. Abrasive portion using diamond dust remove material at a rate determined by grit size and pressure. Abrasive portion using perforations remove material by the interior edges of the perforations acting as planing edges, with removal rate determined by the sharpness of the perforated edge and pressure applied, as well as by the overlap of adjacent perforations and size of the perforations. Larger perforations will remove more material on each pass than smaller perforations.

It will be understood that each of the elements described above, or two or more together may also find useful application in other types of methods differing from the types described above. While the present invention has been described with reference to specific embodiments, it should be understood that it is not intended to be limited to the details described above. Those skilled in the art understand that various alterations, modifications, substitutions, or omissions of the forms and details of the preferred embodiment may be made without departing from the spirit and scope of this prevent invention. Therefore, it should be clearly understood that the descriptions and illustrations of the preferred embodiment are only to facilitate a clearer understanding of the invention and not used to unduly limit the scope of the present invention. Other embodiments are possible, their specific designs depending upon the particular application. As such, the scope of the invention should not be limited by the particular embodiments herein described but should be defined only by the appended claims and equivalents thereof.

I claim:

1. A disposable dental filing tool, comprising:
   a handle including a horizontal arm with a first vertical arm attached at first end and a second vertical arm attached at second end forming an arch structure;
   a filing strip with first and second ends attached to said handle at said first and second vertical arms, suspended therebetween with tension;
   wherein said horizontal arm tapers in thickness to a beveled interior edge;
   wherein each of said vertical arms tapers in thickness inwards to a beveled interior edge; and
   wherein said vertical arms have flattened fingertip end pads to allow for holding the handle between opposing fingertips.

2. A disposable dental filing tool, comprising:
   a handle including a horizontal arm with a first vertical arm attached at first end and a second vertical arm attached at second end forming an arch structure,
   a filing strip with first and second ends attached to said handle at said first and second vertical arms, suspended therebetween with tension; and
   wherein said horizontal arm tapers in thickness to a beveled interior edge;
   wherein said vertical arms have flattened fingertip end pads to allow for holding the handle between opposing fingertips.

3. A disposable dental filing tool of claims 1 or 2, wherein said filing strip is coated entirely with superfine abrasive material.

4. A disposable dental filing tool of claims 1 or 2, wherein said filing strip is partially coated superfine abrasive material.

5. A disposable dental filing tool of claims 1 or 2, wherein said filing strip is coated on one side with superfine abrasive material.

6. A disposable dental filing tool of claims 1 or 2, wherein said filing strip is coated on both sides with superfine abrasive material.

7. A disposable dental filing tool of claims 1 or 2, wherein said filing strip has a sharp cutting edge system.

8. A disposable dental filing tool of claims 1 or 2, wherein said filing strip has sharp-edged perforations along a lateral surface.

9. A disposable dental filing tool of claims 1 or 2, wherein said filing strip is coated with a superfine abrasive material on the middle portion of it.

10. A disposable dental filing tool of claims 1 or 2, wherein the filing strip is provided with saw toothed ends on the top edge and bottom edge of the filing strip.

11. A disposable dental filing tool of claims 1 or 2, wherein each of said filing strip first and second ends is provided with a mounting hole.

12. A disposable dental filing tool of claims 1 or 2, wherein each of said filing strip first and second ends is provided with a mounting hole and an open slot extending from said mounting hole to the respective distal end of said filing strip.

13. A disposable dental filing tool of claims 1 or 2, wherein the vertical arms of the handle component have flat, smoothed surface on the outside of the arms.

14. A disposable dental filing tool of claims 1 or 2, wherein the horizontal arm of the handle from its side middle portion is a raised flat.

15. A disposable dental filing tool of claim 14, wherein the raised flat is provided with indicia.

16. A disposable dental filing tool of claims 1 or 2, wherein said handle is made by injection molding plastic into a mold and said filing strip is attached by forming the ends of the filing strip within the handle during the injection molding process.

17. A dental filing tool as in claims 1 or 2, further comprising:
   wherein said handle further comprises a unitary handle, formed from injection-molded plastic, and each of said first and second vertical arms includes a corresponding projecting end distal from said horizontal arm; and,
   wherein said filing strip further includes front and back surfaces, first and second mounting holes at the corresponding distal ends of said filing strip, and abrasive means disposed along said filing strip; and,
   wherein, said filing strip first and second ends are attached to said first and second vertical arms by embedding said filing strip first and second ends, including said first and second mounting holes, within said first and second vertical arm projecting ends, respectively.

18. A dental filing tool as in claim 17, wherein said abrasive means comprises coating at least one of said front and back surfaces with diamond dust in the range of 200 grit to 900 grit.

19. A dental filing tool as in claim 18, wherein said filing strip further includes at least one serrated cutting edge.

20. A dental filing tool as in claim 18, wherein said filing strip further includes an open slot extending from each of said mounting holes to the corresponding extreme distal end of said filing strip.

21. The dental filing tool as in claim 18 wherein said filing strip is selected from the group of materials consisting of stainless steel and titanium with thickness in the range 0.04 mm to 0.12 mm (0.0016 to 0.0047 inches).

22. A dental filing tool as in claim 17, wherein said abrasive means comprises a pattern of sharp-edged perforations through said filing strip distributed along the length of said filing strip.

23. A dental filing tool as in claim 22, wherein said sharp-edged perforations are round.

24. A dental filing tool as in claim 22, wherein said sharp-edged perforations are diamond-shaped.

25. A dental filing tool as in claim 22, wherein said sharp-edged perforations are rectangular.

26. A dental filing tool as in claim 22, wherein said pattern includes alternating groupings of round and diamond-shaped sharp-edged perforations.

27. A dental filing tool as in claim 22, wherein said pattern of sharp-edged perforations comprises a combination of one or more perforation shapes selected from the group consisting of round, diamond and rectangular.

28. A dental filing tool as in claim 22, wherein said sharp-edged perforations are circular.

29. A dental filing tool as in claim 22, wherein said sharp-edged perforations are diamond-shaped.

30. A dental filing tool as in claim 22, wherein said pattern of sharp-edged perforations consists of alternating groupings of circular-shaped and diamond-shaped perforations.

31. A dental filing tool as in claim 22, wherein said sharp-edged perforations are substantially rectangular-shaped.

32. A dental filing tool as in claim 22, wherein said sharp-edged perforations overlap adjacent sharp-edged perforations in the range of one-third to two-thirds of their cross-sections.

33. The dental filing tool as in claim 22 wherein said filing strip is selected from the group of materials consisting of stainless steel and titanium with thickness in the range 0.04 mm to 0.12 mm (0.0016 to 0.0047 inches).

34. A dental filing tool as in claim 17, wherein said abrasive means is limited to the portion of said strip which is not embedded within said plastic handle.

* * * * *